(12) United States Patent
Bahatt et al.

(10) Patent No.: US 8,202,479 B1
(45) Date of Patent: Jun. 19, 2012

(54) LIGHT COLLECTION SYSTEM

(75) Inventors: Dar Bahatt, Foster City, CA (US);
Konrad Faulstich, Fremont, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1518 days.

(21) Appl. No.: 11/270,263

(22) Filed: Nov. 9, 2005

Related U.S. Application Data (60) Provisional application No. 60/626,784, filed on Nov. 9, 2004.

(51) Int. Cl.
*C12M 1/34* (2006.01)

(52) U.S. Cl. .......... 422/82.08; 422/82.05; 422/502; 422/503; 422/504; 422/508; 257/183; 257/184; 438/16; 438/456; 138/140; 138/141; 136/243; 136/255

(58) Field of Classification Search .......... 422/82.08, 422/82.05, 502–504, 507; 138/140, 141; 257/183, 184; 438/16, 456; 136/43, 255
See application file for complete search history.

(56) References Cited

U.S. PATENT DOCUMENTS

| | | | | |
|---|---|---|---|---|
| 5,212,394 | A * | 5/1993 | Iwasaki et al. | 428/66.7 |
| 5,416,879 | A | 5/1995 | Liu | |
| 5,798,032 | A | 8/1998 | Khan et al. | |
| 5,846,708 | A | 12/1998 | Hollis et al. | |
| 6,630,307 | B2 * | 10/2003 | Bruchez et al. | 506/17 |
| 6,682,942 | B1 | 1/2004 | Wagner et al. | |
| 6,858,876 | B2 * | 2/2005 | Gordon et al. | 257/96 |
| 7,051,945 | B2 * | 5/2006 | Empedocles et al. | 235/492 |
| 2002/0092987 | A1 * | 7/2002 | Cho et al. | 250/338.4 |
| 2003/0024635 | A1 * | 2/2003 | Utsunomiya | 156/272.2 |
| 2005/0127363 | A1 * | 6/2005 | Nishiki et al. | 257/72 |
| 2007/0003948 | A1 * | 1/2007 | Brogan et al. | 435/6 |
| 2010/0326429 | A1 * | 12/2010 | Cumpston et al. | 126/710 |

* cited by examiner

*Primary Examiner* — In Suk Bullock
*Assistant Examiner* — Timothy G Kingan (57) ABSTRACT

The present teachings provide a detection cell for a biological material and methods for detecting biological material including a photosensitive material optically coupled to an interior volume containing the biological material so to avoid optical components or an external light source.

17 Claims, 5 Drawing Sheets

FIG. 9

LIGHT COLLECTION SYSTEM

CROSS-REFERENCE TO RELATED APPLICATIONS

This application claims a priority benefit under 35 USC §119(e) from U.S. Patent Application No. 60/626,784 filed Nov. 9, 2004, which is incorporated herein by reference.

FIELD

The present teaching relate to methods and systems for detection of biological samples.

INTRODUCTION

Detection of results from assays on biological samples is usually done by detection of emission light from the biological samples. Typically, excitation light is provided by an external light source to excite a moiety of the biological sample to provide emission light. The direction of excitation light to the biological sample from the external light source and the direction of emission light to a detector from the biological sample require optical components to direct the light, such as lenses, mirrors, gratings, prisms, etc. External light source and associated optical components add complexity and size to detection systems. It is desirable to select assays for the biological samples that do not use external light sources and associated optical components.

Assays that do not use external light sources and associated optical components provide results in the form of luminescent light. Luminescent light originates from inside the biological sample. Since excitation light does not have to reach the biological sample detection can occur in the vicinity of the biological sample. It is desirable to provide detection of the luminescent light in the vicinity of the sample. Collection of the luminescent light can be provided by the container of the biological material. It is desirable to provide a container that collects the luminescent light for detection in the vicinity of the sample.

SUMMARY

In various embodiments, the present teachings provide a detection cell for a biological material including an interior volume adapted to contain the biological material, and a photosensitive material optically coupled to the interior volume, the photosensitive material being adapted to detect light emitted from the biological material in the interior volume.

In various embodiments, the present teachings provide a method for detection of a biological material including transporting the biological material to an interior volume, emitting light from a luminescent reaction of the biological material, and detecting the light emitted from the biological material in an interior volume of the detection cell, wherein the light is emitted without an external light source.

Some advantages of the present teaching will be set forth in part in the description which follows, and in part will be obvious from the description, or may be learned by practice of the various embodiments. The advantages of the embodiments will be realized and attained by means of the elements and combinations particularly pointed out in the appended claims.

It is to be understood that both the foregoing general description and the following detailed description are exemplary and explanatory only and are not to be restrictive of the embodiments, as claimed.

The accompanying drawings, which are incorporated in and constitute a part of this specification, illustrate several embodiments and together with the description, serve to explain the principles of the present teaching.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

It is to be understood that both the foregoing general description and the following detailed description are exemplary and explanatory only, and are intended to provide an explanation of various embodiments of the present teachings.

DESCRIPTION OF THE EMBODIMENTS

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose. In the event that one or more of the incorporated literature and similar materials differs from or contradicts this application, including but not limited to defined terms, term usage, described techniques, or the like, this application controls.

The term "optically coupled" as used herein refers to the ability to propagate light without the used of optical components to direct the light, such as lenses, mirrors, gratings, prisms, etc. According to the present teachings, the interior volume containing the biological material or the container walls are not optical components, but can be used to channel the emission light from the biological material to the photosensitive material.

The term "external light source" as used herein refers to a source of irradiance that can provide excitation that results in fluorescent emission. External light sources can include, but are not limited to, white light, halogen lamp, laser, solid state laser, laser diode, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, an ensemble of LEDs, a floodlight system using LEDs, and/or white LEDs, filament lamps, arc lamps, gas lamps, and fluorescent tubes. External light sources can have high irradiance, such as lasers, or low irradiance, such as LEDs. The different types of LEDs mentioned above can have a medium to high irradiance.

The term "photosensitive material" as used herein refers to any component, portion thereof, or system of components that can interact with, alter the path of, and/or detect light including a reflective material, mirror, charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, an avalanche diode structure, a charge-injection device (CID), CID arrays, etc. The detector can be adapted to relay information to a data collection device for storage, correlation, and/or manipulation of data, for example, a computer, or other signal processing system.

Photosensitive material can provide multi-color detection by multi-layered material with each layer sensitive to a different color. For example, the color photodetectors organized in three layers within a sensor to form full-color pixels (Foveon, Inc., Santa Clara, Calif.). By dedicating three color photodetectors for each pixel, images are sharper, have better color detail, and are more immune to color artifacts. Alternatively, photosensitive material in multi-color photodiodes can provide multi-color detection. Examples of such photodiodes include those based on silicon and gallium arsenic.

The term "interior volume" as used herein refers to any structure, such as a sample region, channel, micro-fluidic channel, or chamber that provides containment for a sample, such as a biological material in a liquid or solid sample. The interior volume can be bounded by walls that can be opaque or transparent and can include a semiconductor material, such as silicon, germanium, silicon germanium, gallium arsenide, etc.; or an insulator, such as glass, $SiO_2$, fused silica, etc.; polymers, or an organic-inorganic hybrid material.

In various embodiments, an organic-inorganic hybrid material for containing a solid sample can be one obtained by a sol-gel method. In such embodiments, the interior volume can be bound by a sol-gel or the interior volume itself can be a sol-gel. Examples of sol-gels include those using precursors such as 3-trimethoxysilylpropyl methacrylate (MPTS, $H_2C=C(CH_3)CO_2(CH_2)_3Si(OCH_3)_3$, made by Aldrich Chemical) and heptadecafluorodecyl trimethoxysilane (PFAS, $CF_3(CF_2)_7(CH_2)_2Si(OCH_3)_3$, made by Toshiba). The two precursors, MPTS and PFAS, can be mixed with water in presence of 0.05N hydrochloric acid (HCl) as a catalyst for sol-gel reaction. After stirring the solution of MPTS(3), PFAS (1) and water(2) in the presence of 0.05N HCl (where the bracketed numbers indicate molar equivalents) for 9 hours at 60° C., a totally transparent solution can be obtained. Subsequently, the transparent solution can be filtered through a 0.22 μm-size filter to remove impurities and gas bubbles. The filtered solution can be kept still for 30 minutes to remove gas bubbles resulting from the stirring and filtering. The filtered solution can be used as the internal volume where biological samples filter in via diffusion. Alternatively, the filtered solution can be used to coat the boundary of the internal volume. For example, the sol-gel can be coated onto a p-doped Si(100) wafer by spin-coating at 2000 rpm for 30 seconds. Finally, the coated film can then be cured thermally for 12 hours at 150° C. UV (200-260 nm) by light irradiation, using for example, a Oriel 82511 Hg/Xg lamp, which gives a power density of 45 $mJ/cm^2$.

Further, the interior volume can take any shape including a well, a tube, a channel, a micro-fluidic channel, a vial, a cuvette, a capillary, a cube, an etched channel plate, a molded channel plate, an embossed channel plate, etc. The interior volume can be part of a combination of multiple interior volumes grouped into a row, an array, an assembly, etc. Multi-chamber arrays can include 12, 24, 36, 48, 96, 192, 384, or more, interior volume chambers.

The term "biological material" as used herein refers to any biological or chemical substance, alone or in solution, with components that can emit light in a liquid sample or solid sample. Examples of luminescent moieties that can be included in biological material are listed in Table 1 with emission wavelengths and fluorescent concentrations (Albrecht, Steffen, et al. Chemiluminescence: Reaction systems and their application under special consideration of biochemistry and medicine, Huthig GhbH, Heidelberg, Germany, pp. 9-10, 1996):

TABLE 1

| Luminescent Moiety | Emission Wavelength (max. in nm) | $\phi_{CL}$ (Einstein/mol) |
| --- | --- | --- |
| Luminol | 424 | 0.01 |
| Isoluminiol | 425 | 0.001 |
| Lucigenin | 530 | 0.02 |
| Aryloxalate + Fluorescer | — | 0.05-0.50 |
| p-Chlorophenyl Magnesium Bromide | 475 | $10^{-6}$-$10^{-8}$ |
| Bacterial Luciferine/ Luciferasen | 460-480 | 0.05-0.30 |
| Aequorin | 469 | 0.15-0.20 |
| Pholasin | 495 | 0.10 |
| Firefly Luciferine/ Luciferase | 565 | 0.90 |
| Adamantandioxetane | 477 | $10^{-4}$ (in DMSO bis 0.20) |

The biological material can include luminescent labels that can combine with luminescent moieties in a detection reaction or can be luminescent themselves to provide detection of certain analytes in the biological material; examples of which are listed in Table 2 showing examples of luminescence including chemiluminescence (CL) and bioluminescence (BL) (Albrecht, Steffen, et al. Chemiluminescence: Reaction systems and their application under special consideration of biochemistry and medicine, Huthig GmbH, Heidelberg, Germany, pp. 35-36, 1996):

TABLE 2

| Luminescent Label | Detection Reaction | Analyte |
|---|---|---|
| Acridiniumester | $+H_2O_2/OH \rightarrow CL$ | $T_3$, $T_4$, TSH, $FT_3$, $FT_4$, CKMB, Ferritin, βHCG, PSA, Vit. $B_{12}$, auto-Thyroid AK, Folsr., LH, FSH, Prolactin, HGH, PTH, Cortisol |
| Aequorin | $+Ca^{2+} \rightarrow BL$ | Progesteron, Transferrin |
| Alkaline Phosphatase | $+AMPPD \rightarrow CL$ | AFP, CA 125, CA 19-9, CA 15-3, TSH, LH, HGH, Thyroid diagnostics, Fertility, Anemia |
| ATP | Firefly Luciferin-Luciferase$^+ \rightarrow$ BL | $T_4$, Myoglobin |
| β-Galactosidase, γ-Cyclodextrin | sensing | $T_4$ |
| Glucoseoxidase | Peroxyoxalate-CL $H_2O_2$ by Peroxyoxalate-CL in aqueous solution | Glucose |
| Firefly Luciferase | BL | Methotrexat |
| Fluorescin | Peroxyoxalate-CL | IgG |
| Rhodamin | Peroxyoxalate-CL | LDL |
| Glucoseoxidase | $H_2O_2$ by Peroxyoxalate-CL | 17-Hydroxyprogesteron |
| Glucose-6-phosphate hydrogenase | NAD(P)H-dependent BL | Progesteron, LH, Prolactin, AFP |
| Haemin | Catalysis of Luminol-CL | β2-Microglobulin |
| Horseradish-Peroxidase | Catalysis of Luminol-CL | AFP, CEA, Ferritin, LH, FSH, Progesteron, $T_3,T_4$, $FT_3$, $FT_4$, TSH, TBG, Cortisol, Estriol, Estradiol |
| Horseradish-Peroxidase | Catalysis of Acridanoxidation | Thyroid diagnostics, Blot techniques |
| Luminol- or Isoluminol derivative | $H_2O_2/$ Catalyst $\rightarrow$ CL | Thyroid diagnostics, Fertility, Tumor marker, Reproduction, Cortisol, Progesteron |
| Bacterielle Luciferase | BL | Immuoglobuline |
| NAD$^+$ | BL | Estriol |
| Pyruvatkinase | ATP-dependent Firefly-BL | Transferrin, Insulin |
| Xanthinoxidase | $H_2O_2$-generation + Luminol $\rightarrow$ CL | IgE, Prolactin, $T_4$, TSH |

Examples of these luminescent labels and luminescent moieties in biological material are manufactured by companies like Byk Sangtec, Ciba Corning, Nichols Diagnostics, Brahms GmbH, Boeringer Mannheim, Millipore, Celcius Limited, and Biotrace Limited. In various embodiments, the luminescent moiety can be dioxetane. Dioxitane can provide a detection reaction with alkaline phosphatase luminescent label. Example of such reactions can detect antibodies in lysed cells (U.S. Pat. No. 6,686,171).

Figure 7:
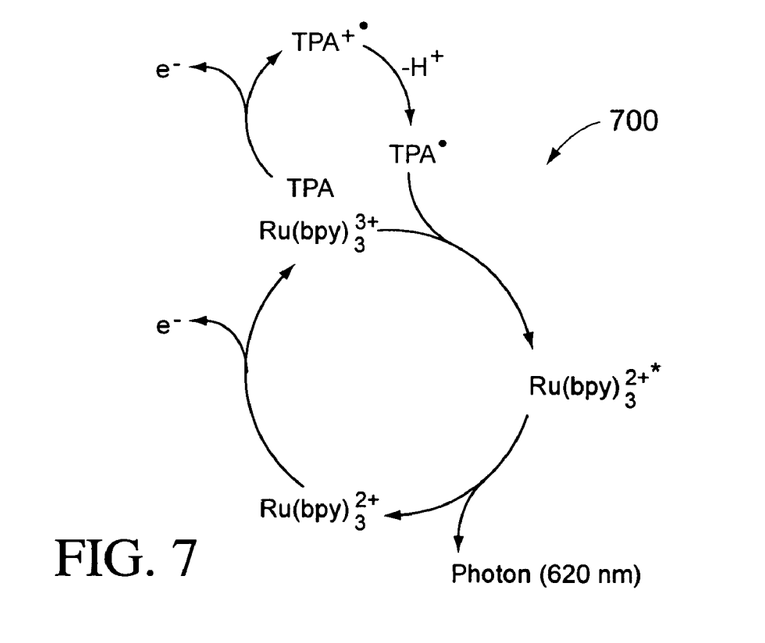
FIG. 7 illustrates an example of an assay that can generate luminescent light.

The biological material can include one or more nucleic acid sequences to be monitored. The biological material can be monitored by polymerase chain reaction (PCR) and other reactions such as ligase chain reaction, antibody binding reaction (immunoassay), oligonucleotide ligations assay, and hybridization assay. In various embodiments, the biological material can also be subjected to thermal cycling or isothermal cycling. In various embodiments, the biological material can be subjected to an electric current. An example of an immunoassay is illustrated by FIG. 7 providing a biological material that can react with an electrode to provide electrochemiluminescence. In various embodiments, the electrode used to generate the electrochemiluminesce can also provide current for manipulating the biological material in a liquid. For example, electrowetting on a diaelectric (U.S. Pat. No. 6,565,727).

The biological material can include a combination of luminescent moieties that generate different and spectrally distinguishable luminescence. For example, the biological sample can include different analytes, labels, and/or luminescent moieties that emit light at different wavelengths to provide multi-color detection. In various embodiments, luminescent moieties can be paired with fluorescent dyes such that emission wavelengths of the luminescent moieties can activate the fluorescent dyes. Such pairing can provide better spectral separation and facilitate multi-color detection for end-point quantitation and/or real-time detection. Examples of fluorescent dyes with desirable excitation and emission wavelengths can include 5-FAM™, SYBR Green, TET™, VIC™, JOE, TAMRA, NED, ROX, CY3, Texas Red, CY5, etc. The present teaching applies at least to red dyes, green dyes, and blue dyes.

The term "refractive material" as used herein refers to any material that can reflect a predetermined wavelength of light. Refractive materials can be metals that reflect all wavelengths. Refractive materials can be a coating, a distinct layer, or a various components described herein can themselves act as a reflective materials. Some exemplary reflective materials include, for example, insulators, such as $SiO_2$, TiN, SiON; semiconductor materials, such as silicon, germanium, silicon germanium, and compound semiconductors; polymers, such as Teflon®, Teflon® AF; an organic-inorganic hybrid material as disclosed above, or any other reflective material that will be known to one of ordinary skill in the art. In various embodiments, the refractive material can permit external light to penetrate the internal volume to manipulate the biological material, but not provide excitation. For example, biological material in liquid can be manipulated by optically activated electrowetting on dielectrics (U.S. Pat. App. 2003/0224528 A1) and optically activated dielectrophoresis (Chiou, P. Y., et al., A Novel Optoelectri Tweezer Using Light Induced Dielectrophoresis, Proceeding of IEEE/LEOS Intl Conf. Optical MEMS, pp 8-9, 2003).

The term "on" as used herein can be any of on an exterior surface, on an interior surface, or inside of a material.

Figure 1:
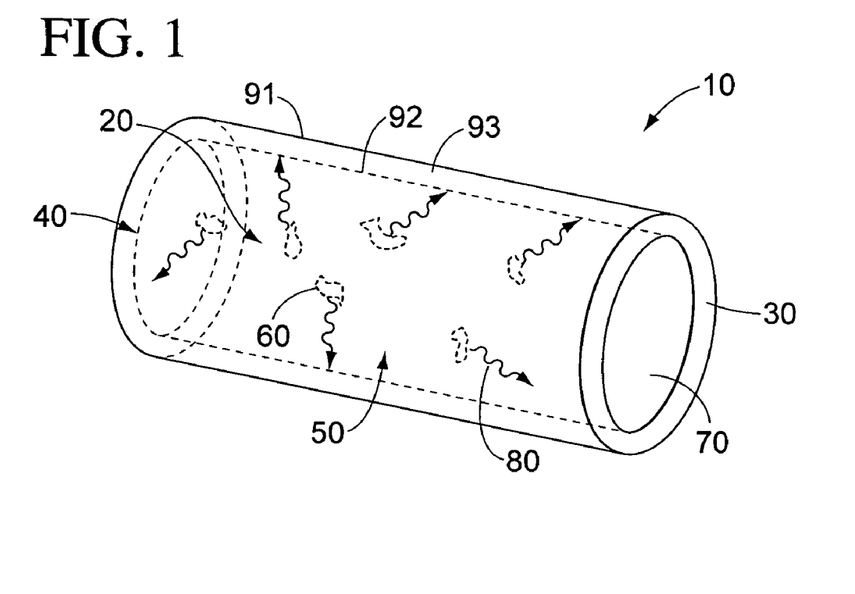
FIG. 1 is a perspective view of a representative biological detection cell according to various embodiments of the present teachings.

An embodiment of the present teaching shown in FIG. 1 includes a detection cell 10 including an interior volume 20, a wall 30, and a photosensitive material 40. Photosensitive material 40 can be optically coupled to interior volume 20. As used herein, the term optically coupled is understood to mean that light emitted in the interior volume 20 is capable of reaching photosensitive material 40. Moreover, interior volume 20 can be adapted to contain a sample, such as a liquid 50 that can be in contact with a biological material 60. Further, in various embodiments, interior volume 20 can include at least one closed end 70. In various embodiments, interior volume 20 can be filed with a solid, such as a sol-gel permitting biological material 60 to diffuse into the sol-gel. The sol-gel can include conditions for the detection reaction, for example, suspension of the luminescent label.

In various embodiments, the biological material 60 can be transported to the interior volume 20 along with the liquid 50 or the liquid 50 can be received by the interior volume 20 separately. When the biological material 60 is in contact with the liquid 50, the biological material 60 can emit light, shown in FIG. 1 with arrows 80. For example, the liquid can contain a luminescent label that causes the detection reaction with an analyte. In this instance, the biological material is both the analyte before the detection reaction, the reaction complex of analyte with luminescent label and after reacting to produce emission light.

In various embodiments, the biological material can emit either a single or a narrow band of light, or the biological material can emit multiple wavelengths or multiple narrow bands of light. Moreover, in various embodiments, multiple biological materials including multiple analytes, multiple luminescent labels, etc. can be received by the interior volume 20. Multiple wavelengths or multiple narrow bands can be optically coupled to the photosensitive material 40 and can be spectrally resolved by a detector connected to the photosensitive material 40. For example, a first biological material can produce a first wavelength. Similarly, a second biological material can produce a second wavelength. Each of the first and second wavelengths can be optically coupled to the photosensitive material 40 and they can be detected and resolved by a detector (not shown).

In various embodiments, some examples of which will be described below, the photosensitive material 40 can be positioned on interior volume 20. For example, an exterior surface 91, an interior surface 92, and/or the inside 93 of wall 30, can include photosensitive material 40. The photosensitive material 40 can also be positioned on an end 70 of interior volume 20 and/or wall 30. Similarly, "on an end" is understood to be any of on an exterior surface (not shown), an interior surface (not shown), or inside of end 70 (not shown). Further, "on an end" is understood to mean substantially at the end of the interior volume and/or wall 30. For example, the photosensitive material can be positioned such as to provide a gap for liquid to pass from the interior volume to the exterior of the wall, where the gap is sufficiently narrow to permit the interior volume and/or the wall to be optically coupled to the photosensitive material. In certain embodiments, the photosensitive material 40 can be positioned on all or a portion of interior volume 20 and/or wall 30. Further, in various embodiments, photosensitive material 40 can be manufactured to form interior volume 20, end 70, and/or wall 30.

The light from the biological material is emitted within the interior volume 20 without the use of an external light source. In various embodiments, because the biological material is surrounded by the interior volume 20, the photosensitive material will detect a substantial amount of the emitted light. As such, there are smaller losses from embodiments described herein than in other systems.

Figure 2:
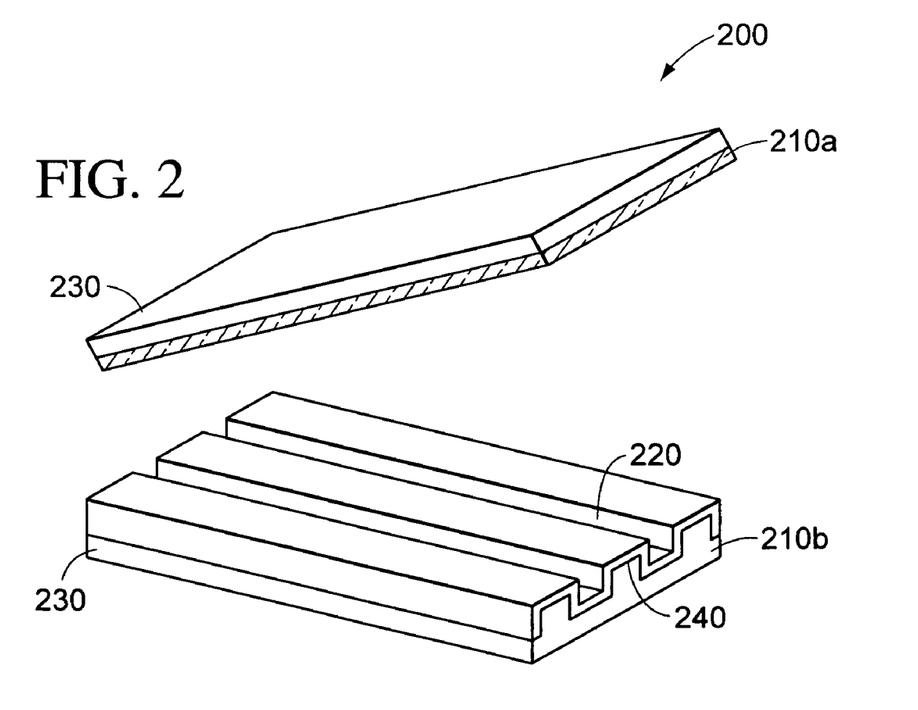
FIG. 2 is a perspective view of a representative biological detection cell according to various embodiments of the present teachings.

In various embodiments there is a detection cell 200, such as a micro-fluidic biological material detector, as shown in FIG. 2, including a first surface 210a and a second surface 210b that when touched together form a sandwich structure. Detection cell 200 also includes an interior volume 220 that can be defined by first surface 210a and second surface 210b. In various embodiments, first surface 210a and second surface 210b can be formed on a wall 230, which serves as a substrate to support the surfaces. Further, in certain embodiments, detection cell 200 can further include an end (not shown) positioned at the end of interior volume 220. Detection cell 200 can also include a photosensitive material 240 optically coupled to interior volume 220 and/or the end of interior volume 220.

In various embodiments at least one of first surface 210a, second surface 210b, and wall 230 can include a semiconductor material, such as silicon, germanium, gallium arsenide, etc.; an insulator, such as $SiO_2$; fused silica; plastic; or any other suitable material that can support interior volume 220. In various embodiments, Teflon® AF can be on the interior volume 220 and/or on wall 230.

In various embodiments, the interior volume can be bound by a flexible sheet film. This film could be thick enough to create the interior volume over a flat substrate. Most existing CCD system are sold with a protective clear material to protect the photosensitive material underneath. Rather than forming the interior volume in the photosensitive material, the interior volume can be shaped by the flexible sheet film to provide optical coupling with the off-the-shelf CCD.

In various embodiments, the luminescent labels can be deposited on the flexible sheet film forming the interior volume such that the biological material emits light from the surface of the flexible sheet. In various embodiments, the photosensitive material can be positioned to be proximate to the location on the flexible sheet film where the luminescent labels are located to provide increased collection of emission light.

In various embodiments, the interior volume 220 can be formed in at least one of the first surface 210a and second surface 210b. The interior volume 220 can be formed by standard etching, casting, or molding techniques, or by other techniques as will be known to one of ordinary skill in the art.

In various embodiments, interior volume 220 can serve as a waveguide. For example, the index of refraction of the interior of interior volume 220, and/or its contents, can be greater than the index of refraction of the first surface 210a, second surface 210b, and walls 230. As such, light can be channeled through the waveguide by total internal reflection as will be known to one of ordinary skill in the art.

In various embodiments, at least one of first surface 210a, second surface 210b, wall 230, and the end of interior volume 220 can include various photosensitive materials 240. For example, in an embodiment, first surface 210a and second surface 210b can include a reflective material and the end of interior volume 220 can include the photosensitive material, such as, for example, a CCD structure, a photodiode, or a portion of a photomultiplier tube. In another embodiment, at least one of first surface 210a and second surface 210b can include the photosensitive material 240. It will be understood that various combinations of photosensitive materials 240 can be used on interior volume 220. A substantial portion of the light emitted inside of interior volume 220 can be optically coupled to the photosensitive material 240.

In various embodiments, the biological material 60 can be transported to the interior volume 220 along with the liquid 50 or the liquid 50 can be received by the interior volume 220 separately. As described above, when the biological material 60 can emit light under the proper conditions. In various embodiments, the biological material can emit either a single or a narrow band of light, or the biological material can emit multiple wavelengths or multiple narrow bands of light. Moreover, in various embodiments multiple biological materials can be received by the interior volume 220. Multiple wavelengths or multiple narrow bands can be optically coupled to the photosensitive material 240 and can be spectrally resolved by a detector connected to the photosensitive material 240. For example, a first biological material can produce a first wavelength. Similarly, a second biological material can produce a second wavelength. Each of the first and second wavelengths can be optically coupled to the photosensitive material 240 and they can be detected and resolved by a detector (not shown).

The biological material 60 and the liquid 50 are surrounded by the interior volume 220. A substantial amount of the emitted light is contained inside interior volume 220 is detected by the photosensitive material 240. In situations where one of first surface 210a and second surface 210b includes a reflective or refractive material, the light emitted by the of biological material 60 is reflected or refracted back inside of interior volume 220 and is detected by photosensitive material 240.

In various embodiments, after the emitted light has been monitored, the liquid sample 50 and the biological material 60 can be purged from the detection cell 200.

Figure 3:
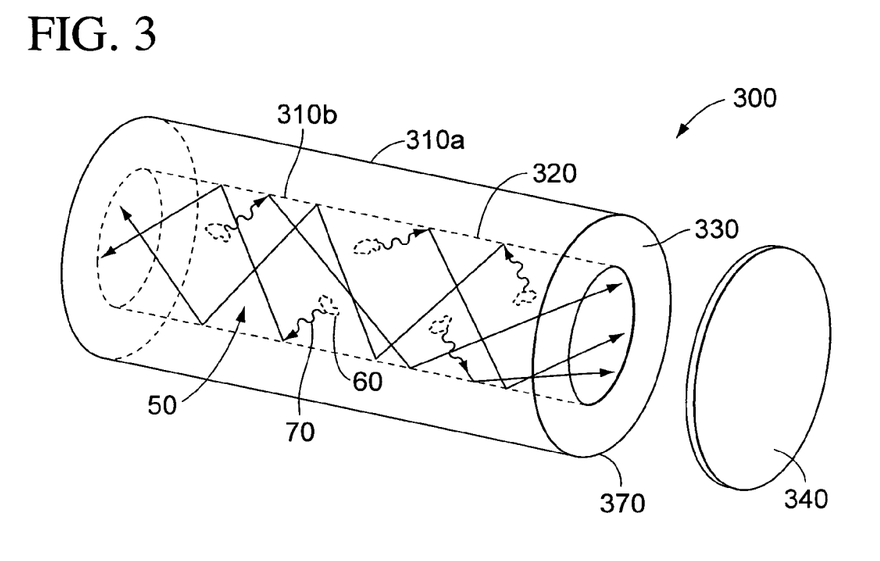
FIG. 3 is a perspective view of a representative biological detection cell according to various embodiments of the present teachings.

In various embodiments, there is a detection cell 300, such as a micro-fluidic biological material detector, as shown in FIG. 3, including a light channeling structure 330, such as the wall of a tube surrounding an interior volume 320. The light channeling structure 330 further includes a first surface 310*a* around a second surface 310*b*. The detection cell 300 further includes a photosensitive material 340, such as, for example, a CCD, a photodiode, or a photomultiplier tube, positioned on at least an end 370 of the interior volume 320.

It is to be understood that the light channeling structure 330 can assume any applicable shape. For example, the light channeling structure can be a cylindrical, rectangular, square, oval, etc. Further, the light channeling structure can have a uniform diameter or it can be tapered. Moreover, the light channeling structure can include any of silica, $SiO_2$, plastic, or any suitable waveguide material. In various embodiments, the light channeling structure can be mounted onto a substrate.

In various embodiments, the interior volume 320 and/or its contents, can include a first refractive index, and the light channeling structure 330 can include a second refractive index. In general, the first and second refractive indexes are adjusted such that light inside the channel is internally reflected within the interior volume 320.

In various embodiments, at least one of the first surface 310*a* and the second surface 310*b* can include a reflective material such that light impinging the reflective material from inside the interior volume 320 is reflected back inside the interior volume. In an embodiment, a reflective material can be on the first surface 310*a*. In this case, light emitted from the interior volume 320 can be transmitted through the second surface 310*b*. Upon reaching the first surface 310*a*, the light is sent back into the interior volume 320. In another embodiment, a reflective material can be on the second surface 310*b*. In this case, light emitted in the interior volume 320 that reaches the second surface 310*b* is sent back into the interior volume 320. In yet another embodiment, the material of the light channeling structure 330 between the first surface 310*a* and the second surface 310*b* can include a graded refractive index. In this case, light having a particular wavelength can be sent back into the interior volume 320. In any case, light sent back into the interior volume 320 can be channeled through the interior volume 320. A substantial portion of the light emitted inside of interior volume 320 can be optically coupled to the photosensitive material 340 and the light can be detected by a detector (not shown) coupled to the photosensitive material 340.

In various embodiments, the biological material 60 can be transported to the interior volume 320 along with the liquid 50, or the liquid 50 can be received by the interior volume 320 separately. As described above, when the biological material 60 can emit light. In various embodiments, the biological material can emit either a single or a narrow band of light, or the biological material can emit multiple wavelengths or multiple narrow bands of light. Moreover, in various embodiments, multiple biological materials can be received by the interior volume 320. In either case, when multiple wavelengths or multiple narrow bands are emitted, they can be spectrally resolved by a detector connected to the photosensitive material 340. For example, a first biological material can produce a first wavelength. Similarly, a second biological material can produce a second wavelength. Each of the first and second wavelengths can be optically coupled to the photosensitive material 340 and they can be detected and resolved by a detector (not shown).

Light emitted by the biological material can be channeled through the waveguide formed by interior volume 320 and can be detected by the photosensitive material 340. Because the biological material 60 and the liquid 50 is surrounded by the interior volume 320, a substantial amount of the emitted light can be contained inside interior volume 320 and sent to the photosensitive material 340 for detection. In situations where one of first surface 310*a* and second surface 310*b* includes a reflective material, the light emitted by the biological material 60 and liquid 50 is sent back to interior volume 320 and is detected by photosensitive material 340.

In various embodiments after the emitted light has been monitored, the liquid 50 and the biological material 60 can be purged from the detection cell 300.

Figure 4:
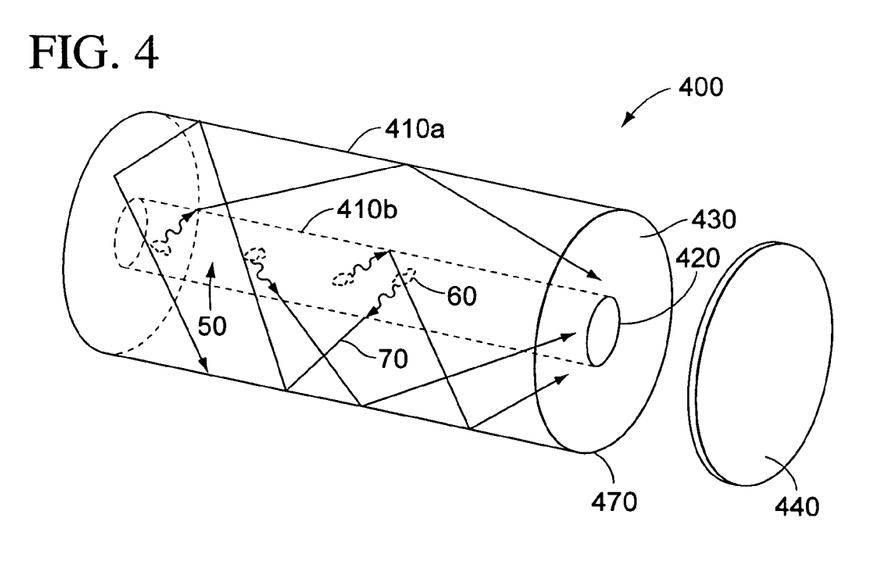
FIG. 4 is a perspective view of a representative biological detection cell according to various embodiments of the present teachings.

In various embodiments there is detection cell 400, such as a micro-fluidic biological material detector, as shown in FIG. 4 including a light channeling material 430, such as the wall of a tube surrounding an interior volume 420. The light channeling material 430 further includes a first surface 410*a* around a second surface 410*b*. The detection cell 400 further includes a photosensitive material 440, such as a CCD, a photodiode, or a photomultiplier tube positioned on and optically coupled to at least an end 470 of the interior volume 420.

It is to be understood that the light channeling material 430 can assume any applicable shape. For example, the light channeling material 430 can be a cylindrical, rectangular, square, oval, etc. Further, the light channeling material can have a uniform diameter or it can have tapering. Moreover, the light channeling material can include any of silica, $SiO_2$, plastic, or any suitable waveguide material. In various embodiments, the light channeling material 430 can be mounted onto a substrate (not shown).

In various embodiments, the interior volume 420 and/or its contents can include a first refractive index, and the light channeling material can include at least a second refractive index. In general, the first and second refractive indexes are adjusted such that light inside the interior volume 420 is transmitted through the second surface 410*b* and is internally reflected by the first surface 410*a* such that the light is internally reflected and stays within the light channeling material 430.

For example, in various embodiments, a reflective material can be on the first surface 410*a*. In this case, light emitted from the interior volume 420 can be transmitted through the second surface 410*b*. Upon reaching the first surface 410*a*, the light is internally reflected back into the wall of the light channeling material 430. In another embodiment, a reflective material can be on the second surface 410*b*. In this case, light emitted in the interior volume 420 that reaches the second surface 410*b* initially transmits through the second surface 410*b* and is confined within the light channeling material 430 between the first surface 410*a* and the second surface 410*b*. In yet another embodiment, the light channeling material 430 between the first surface 410*a* and the second surface 410*b* can include a graded refractive index. In this case, as will be understood by one of ordinary skill in the art, particular wavelengths of light can be confined to different distances between the first surface 410*a* and the second surface 410*b*. In any case, light confined within the light channeling material 430 can be channeled through the light channeling material 430 and the light can be detected by the photosensitive material 440.

In various embodiments, the biological material 60 can be transported to the interior volume 420 along with the liquid 50, or the liquid 50 can be received by the interior volume 420 separately. As described above, the biological material 60 can emit light. In various embodiments, the combination can emit either a single or a narrow band of light, or the combination can emit multiple wavelengths or multiple narrow bands of light. Moreover, in various embodiments, multiple biological materials can be received by the interior volume 420. In either case, when multiple wavelengths or multiple narrow bands are emitted, they can be spectrally resolved by a detector connected to the photosensitive material 440.

Light emitted by the biological material can be channeled through the waveguide formed by light channeling material 430 and can be detected by the photosensitive material 440. Because the biological material 60 and the liquid 50 is surrounded by the light channeling material 430, which serves as a waveguide, the emitted light is contained inside light channeling material 430 by total internal reflection. Further, the photosensitive material 440 will detect substantial amounts of the emitted light. In situations where one of first surface 410a and second surface 410b includes a reflective material, the light emitted by the biological material 60 is confined within the light channeling material 430 and is detected by photosensitive material 440.

For example, a first biological material can produce a first wavelength. Similarly, a second biological material can produce a second wavelength. Each of the first and second wavelengths can be optically coupled to the photosensitive material 440 and they can be detected and resolved by a detector (not shown).

In various embodiments, after the emitted light has been monitored, the liquid sample 50 and the biological material 60 can be purged from the detection cell 400.

Figure 5A:
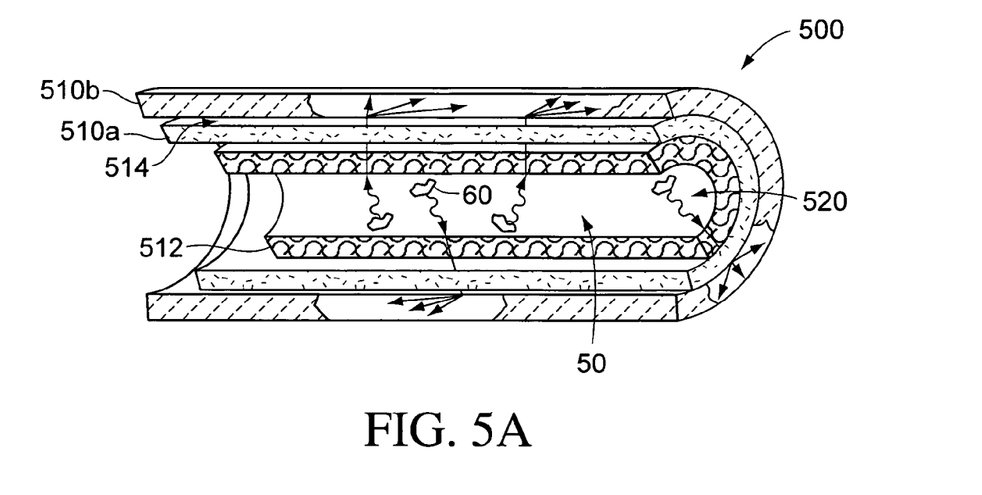
FIG. 5A is a cross-sectional view of a representative biological detection cell according to various embodiments of the present teachings.
Figure 5B:
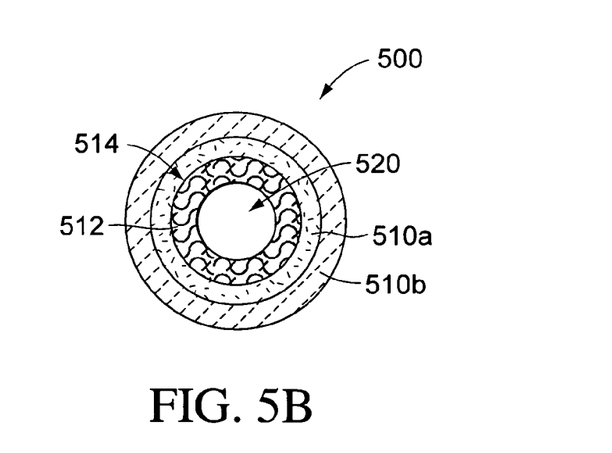
FIG. 5B is a cross-sectional view of a representative biological detection cell according to various embodiments of the present teachings.

In various embodiments, there is a detection cell 500, such as a micro-fluidic biological material detector, as shown in FIGS. 5A and 5B. The detection cell 500 includes a first semiconductor material 510a including a first dopant of a first conductivity type positioned around an interior volume 52. The detection cell 500 further includes a second semiconductor material 510b around the first semiconductor material 510a. The second semiconductor material includes a second dopant of a second conductivity type.

In various embodiments, the first and second semiconductor materials can include silicon, germanium, silicon germanium, compound semiconductor materials such as III-V, and II-VI semiconductors, and any other compound semiconductor material. Further, the first and second dopants can be boron, arsenic, phosphorous, or any semiconductor dopant material that will be known to one of ordinary skill in the art.

In various embodiments, the detection cell 500 further includes an insulating material 512, such as $SiO_x$, GeO, etc., contacting an inner surface 514 of the first semiconductor material. Insulating material 512 can be transparent to certain wavelengths of light emitted in the interior volume 520.

In various embodiments, the first and second semiconductor material 510a and 510b of detection cell 500 can form an avalanche breakdown system. Light emitted in the interior volume 520 can be optically coupled to the interface of the first and second semiconductor materials. For example, light emitted in the interior volume 520 impinging the interface of the first and second semiconductor materials can cause a stimulated emission of electrons. Further, in various embodiments, the detection cell 500 can further include a detector (not shown) coupled to the first and second semiconductor materials adapted to detect stimulated electrons. The detector can generate a data signal that includes information about the stimulated electrons.

In various embodiments, the detection cell 500 can further include a voltage supply (not shown) electrically connected between the first and second semiconductor materials 510a and 510b. The voltage supply can establish a bias, such as a forward bias or reverse bias, between the first and second semiconductor materials that can assist in the generation of the stimulated emission. In various embodiments, the voltage supply can include a piezoelectric element.

It is to be understood that the first and second semiconductor materials can 510a and 510b can assume any applicable shape. For example, the first and second semiconductor materials 510a and 510b can form a cylinder, rectangle, square, oval, etc. Further, the first and second semiconductor materials 510a and 510b can have a uniform diameter or can be tapered. In various embodiments, the first and second semiconductor materials 510a and 510b can be mounted onto a substrate (not shown).

In various embodiments, the biological material 60 can be transported to the interior volume 520 along with the liquid 50, or the liquid 50 can be received by the interior volume 520 separately. The biological material 60 can emit light. In various embodiments, the biological material can emit either a single or a narrow band of light, or the biological material can emit multiple wavelengths or multiple narrow bands of light. Moreover, in various embodiments, multiple biological materials s can be received by the interior volume 520. In either case, when multiple wavelengths or multiple narrow bands are emitted, they can separately stimulate electrons at the interface of the first and second semiconductor materials 510a and 510b.

For example, a first biological material can produce a first wavelength. Similarly, a second biological material can produce a second wavelength. Each of the first and second wavelengths can be optically coupled to the interface to the two semiconductor materials. The wavelengths can then be detected and resolved by a detector (not shown).

Because the biological material 60 and the liquid 50 are surrounded the first and second semiconductor materials 510a and 510b, a substantial amount of the emitted light impinges the interface between the first and second semiconductor materials 510a and 510b.

In various embodiments, after the emitted light has been monitored, the liquid 50 and the biological material 60 can be purged from the detection cell 500.

Figure 6:
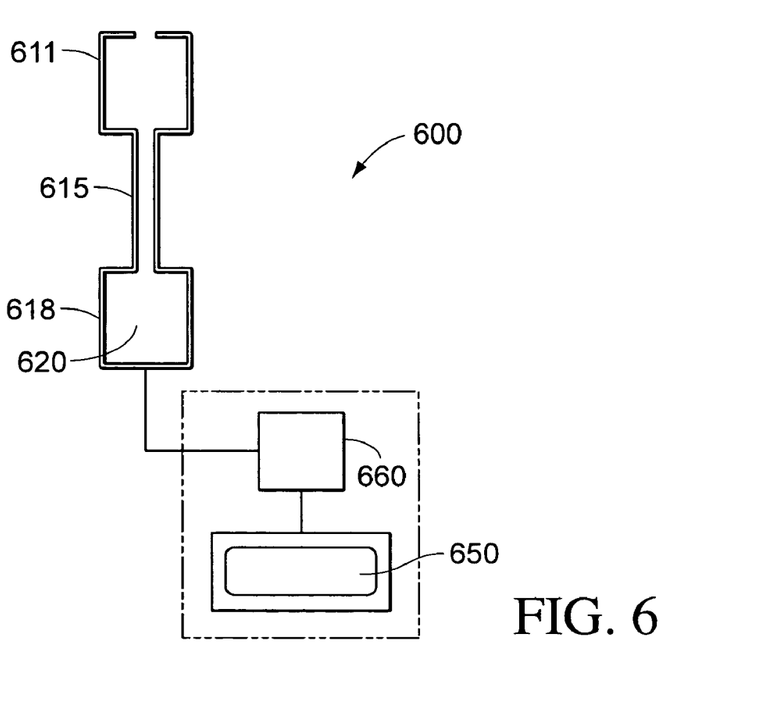
FIG. 6 illustrates a representative biological detection system according to various embodiments of the present teachings.

In various embodiments, there is a biological detection system 600, as shown for example in FIG. 6, including an input port 611, a first channel 615 connected to the input port 611, a detection cell 618 connected to the first channel, and an interior volume 620. The detection cell 618 includes a photosensitive material (not shown). The biological detection system 600 further includes a display 650 that displays a data signal representative of light emitted in the interior volume 620.

In various embodiments, the biological material detection system 600 further includes a processor 660 that processes and converts the signal representative of the emitted light into the data signal that can be displayed on display 650.

In various embodiments, the biological material can be deposited into input port 611 and transported to the detection cell 618 and into interior volume 620 along with a liquid, or the liquid can be received by the interior volume 620 separately. As described above, the biological material can emit light. In various embodiments, the combination can emit either a single or a narrow band of light, or the combination can emit multiple wavelengths or multiple narrow bands of light. Moreover, in various embodiments, multiple biological materials can be received by the interior volume 620. In either case, when multiple wavelengths or multiple narrow bands are emitted, they can be detected by photosensitive material.

For example, a first biological material can produce a first wavelength. Similarly, a second biological material can produce a second wavelength. Each of the first and second wavelengths can be optically coupled to the photosensitive material 440, and they can be detected and resolved by the detection system.

The photosensitive material can generate a signal that is representative of the emitted light. The signal can then be processed by processor 660. Processor 660 then generates a data signal that can be displayed on display 650 in a visual format readable by a user.

EXAMPLE

Figure 8:
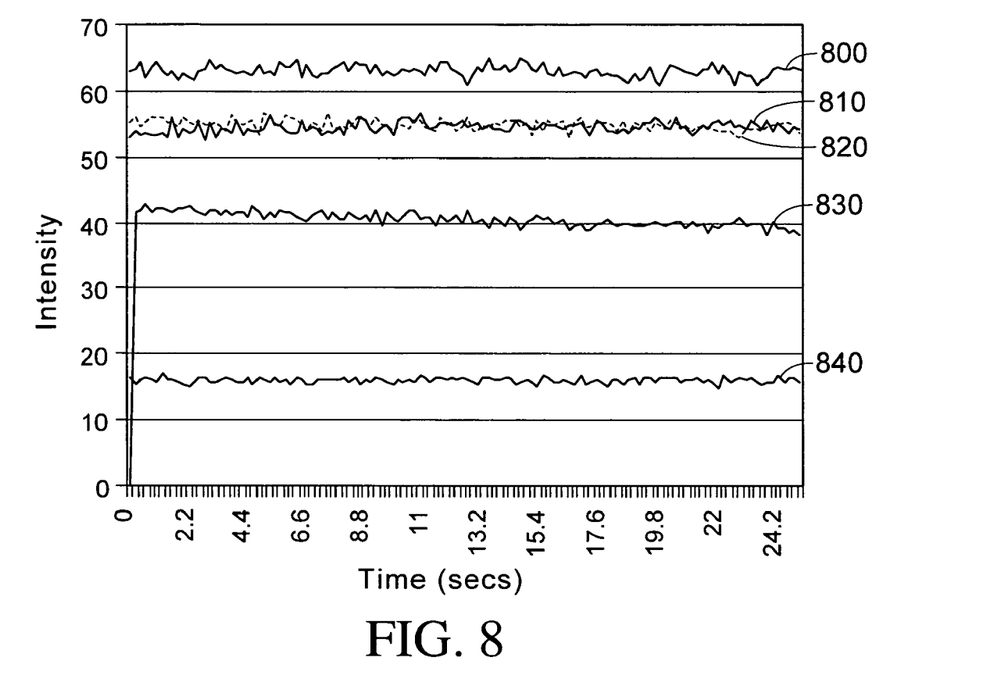
FIG. 8 illustrates a graph showing the intensity of luminescent light detected from different directions relative an internal volume.
Figure 9:
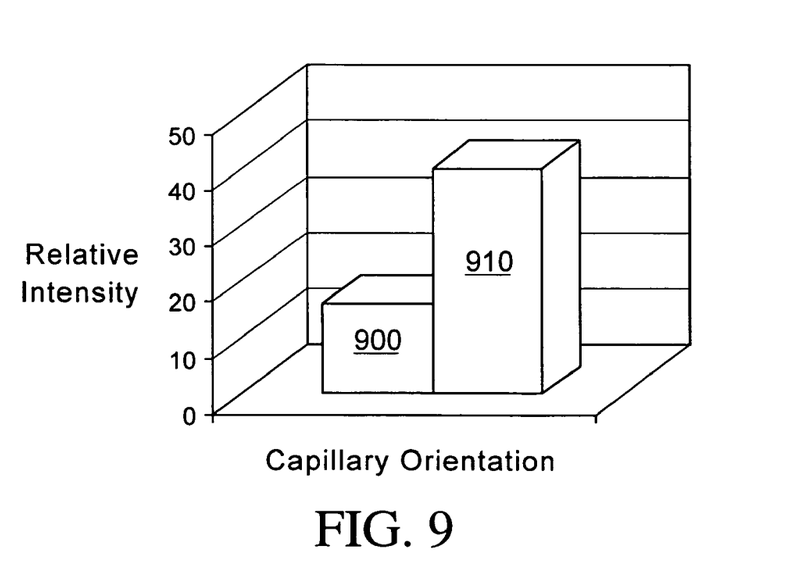
FIG. 9 illustrates a graph showing the relative intensity of luminescent light detection from different directions relative to an internal volume.

FIGS. 8 and 9 show the results of an example of a detection cell for biological material. A 2.5 microliter luminescent reaction was set up containing 2×10-13 moles of pyrophosphate, ATP sulfurlase, adenosine-5'-O-phosphosulfate and luciferase. The reaction was combined in a tube and then introduced into a glass capillary (0.4 mm inside diameter, 0.86 outside diameter, 15 mm in length). Light intensity produced by the reaction was quantified using a Turner TD 20/20 luminometer. Luminescence was measured from five different orientations of the capillary using the same capillary and reaction. Each of the measurements were taking over 25 seconds. FIG. 8 shows the results of intensity over time. The five data sets for the five orientations resulted in line 810 representing light from capillary wall and ends, line 830 representing light from one end of the capillary, line 840 representing light from the capillary wall only (ends taped with black tape), line 820 representing light from one end of the capillary (capillary wall covered by reflective tube holder), line 800 representing light from the capillary wall (ends taped with black tape and covered by reflective tube holder). The data from the chart of FIG. 8 is adjusted to determine the light emission detected by the PMT as relative intensity versus capillary orientation. FIG. 9 shows the average real-time data stream over the 25 seconds. The relative intensity block 900 representing the light from the capillary wall was significantly less than the relative intensity block 910 representing the light from one capillary end. Hence, the capillary was able to act as a light guide and concentrate the emission light to ends of the capillary.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a photosensitive material" includes two or more photosensitive materials. Furthermore, the use of the term "including", as well as other forms, such as "includes" and "included", is not limiting.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A biological material detector adapted to detect light emitted from a biological material, comprising:
   a channel;
   a first semiconductor material surrounding the channel, the first semiconductor material comprising a first dopant; and
   a second semiconductor material disposed about a perimeter of the first semiconductor material, the second semiconductor material comprising a second dopant;
   wherein the channel is configured to receive a biological material and to cause stimulated emission from the biological material to impinge an interface between the first semiconductor material and the second semiconductor material.

2. The biological material detector of claim 1 further comprising: an insulating layer contacting an inner surface of the first semiconductor material.

3. The biological material detector of claim 1 further comprising: a voltage supply electrically connected to the first semiconductor material and the second semiconductor material.

4. The biological material detector of claim 3, wherein the voltage supply comprises a piezoelectric element.

5. The biological material detector of claim 2 further comprising: a plurality of target sites contacting the insulator layer, the target sites comprising a reagent that induces the biological material to emit light.

6. The biological material detector of claim 1, wherein the detector generates a first data signal representative of a first wavelength, wherein the first wavelength is produced by a first biological material being exposed to a first reagent and further wherein the detector generates a second data signal representative of a second wavelength, wherein the second wavelength is produced by a second biological material being exposed to a second reagent.

7. The biological material detector of claim 1, wherein the channel is disposed about an axis and comprises a cross-sectional outer perimeter that is closed in a plane perpendicular to the axis.

8. The biological material detector of claim 1, further comprising a biological material disposed inside the channel, wherein the biological material emits light without the use of an external light source.

9. The biological material detector of claim 1, further comprising a detector configured to detect the stimulated emission.

10. The biological material detector of claim 1, wherein second semiconductor material surrounds the first semiconductor material.

11. A biological material detector, comprising:
    a channel disposed about an axis;

a first semiconductor material surrounding the axis, the first semiconductor material comprising a first dopant; and a second semiconductor material disposed about the first semiconductor material, the second semiconductor material comprising a second dopant;

a biological material disposed inside the channel and emitting light;

wherein the channel is configured to cause stimulated emission from the biological material to impinge an interface between the first semiconductor material and the second semiconductor material.

12. The biological material detector of claim 11, further comprising a detector configured to detect the stimulated emission.

13. The biological material detector of claim 11, wherein second semiconductor material surrounds the first semiconductor material.

14. The biological material detector of claim 11, wherein the biological material emits light without the use of an external light source.

15. A biological material detector, comprising:

a channel disposed about an axis;

a first semiconductor material surrounding the axis, the first semiconductor material comprising a first dopant; and a second semiconductor material disposed about the first semiconductor material, the second semiconductor material comprising a second dopant;

wherein the channel is configured to receive a biological material and to cause stimulated emission from the biological material to impinge an interface between the first semiconductor material and the second semiconductor material.

16. The biological material detector of claim 15, further comprising a detector configured to detect the stimulated emission.

17. The biological material detector of claim 15, wherein second semiconductor material surrounds the first semiconductor material.

* * * * *